(12) United States Patent
Guhaniyogi et al.

(10) Patent No.: US 11,456,075 B2
(45) Date of Patent: Sep. 27, 2022

(54) IMPLANTABLE MEDICAL DEVICE HAVING A CODING MODULE

(71) Applicant: BIOTRONIK SE & Co. KG, Berlin (DE)

(72) Inventors: Shayan Guhaniyogi, Portland, OR (US); Garth Garner, Tigard, OR (US); Martin Li, Sugar Land, TX (US); Jon Nels Peterson, Lake Oswego, OR (US); R. Hollis Whittington, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 180 days.

(21) Appl. No.: 16/893,645

(22) Filed: Jun. 5, 2020

(65) Prior Publication Data

US 2021/0383920 A1 Dec. 9, 2021

(51) Int. Cl.
*A61B 5/00* (2006.01)
*G16H 40/63* (2018.01)
*G06N 20/00* (2019.01)
*A61B 5/316* (2021.01)

(52) U.S. Cl.
CPC ........... *G16H 40/63* (2018.01); *A61B 5/0006* (2013.01); *A61B 5/316* (2021.01); *G06N 20/00* (2019.01)

(58) Field of Classification Search
CPC ......... A61B 5/0006; A61B 5/29; A61B 5/316; A61B 5/686; A61B 5/7232; G06N 20/00; G16H 40/63; G16H 40/40
See application file for complete search history.

(56) References Cited

U.S. PATENT DOCUMENTS

| 5,836,982 A | 11/1998 | Muehlenberg et al. |
| 2018/0182491 A1* | 6/2018 | Belliveau ............... G16H 50/30 |
| 2019/0140658 A1* | 5/2019 | Cooper ................. H03M 7/405 |

FOREIGN PATENT DOCUMENTS

EP 0884851 A2 12/1998

* cited by examiner

*Primary Examiner* — George Manuel
(74) *Attorney, Agent, or Firm* — Laurence A. Greenberg; Werner H. Stemer; Ralph E. Locher

(57) ABSTRACT

An implantable medical device includes an electronic processing device configured for processing a physiological signal, a memory, and a communication device for communicating with an external device. The processing device includes a coding module for coding the physiological signal to obtain an output signal for transmission by the communication device to the external device. The coding module is configured to encode the physiological signal using at least one fixed Huffman code table stored in the memory to obtain the output signal.

18 Claims, 5 Drawing Sheets

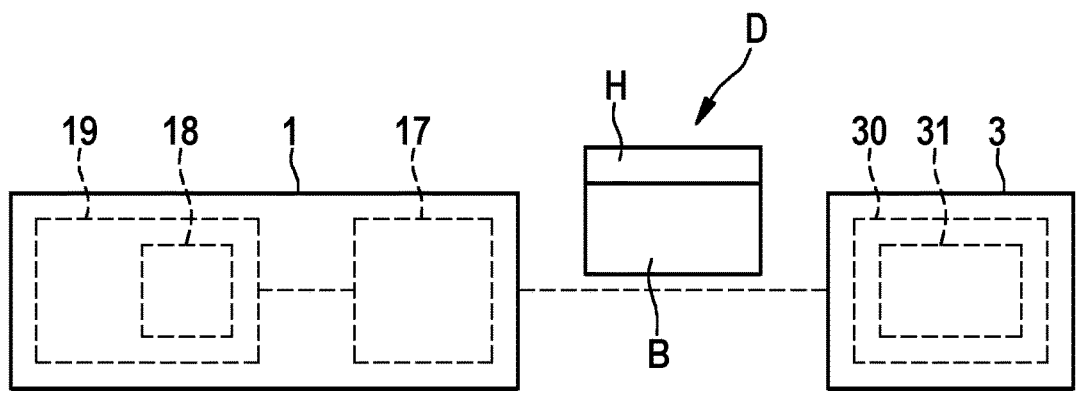
FIG. 6
| Value | Code |
|-------|------|
| 0 | 1 |
| 1 | 01 |
| 2 | 001 |
| 3 | 000 |
FIG. 7
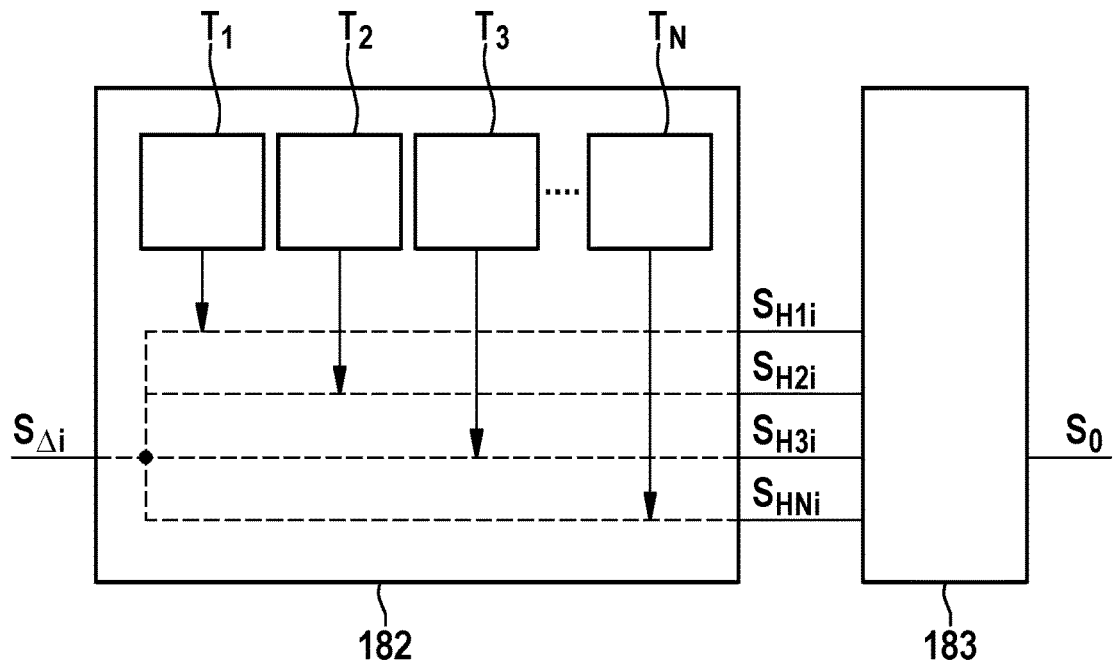
FIG. 8

IMPLANTABLE MEDICAL DEVICE HAVING A CODING MODULE

BACKGROUND OF THE INVENTION

Field of the Invention

The present invention pertains to an implantable medical device, to an external device for communicating with the implantable medical device, and to a method for operating the implantable medical device.

In particular, the present text concerns a low-power implantable medical device which comprises an electronic processing device for processing a physiological signal, a memory device, and a communication device for communicating with an external device. The processing device comprises a coding module for coding the physiological signal to obtain an output signal for transmission by the communication device to the external device.

Such an implantable medical device may for example be a sensing system that can be implanted in a patient's vessel, for example to measure a parameter such as a blood pressure or a blood flow within the vessel. The sensing system can be used to monitor a patient's physiological condition, for example for observing and diagnosing a course of disease, wherein the implantable medical device may be designed to communicate with an external device (located outside the patient) to transmit the measurement results to the external device after measurement by the implantable medical device. In another embodiment, the implantable medical device may be designed as an implantable stimulation device, for example with a pacemaker or neuro-stimulation function, or a diagnostic device.

A physiological signal obtained by means of the implantable medical device generally is a signal which is physiologically obtained using a suitable sensor device, such as a pressure sensor, an accelerometer, an electrode arrangement for sensing electrical signals or the like. The physiological signal accordingly relates to a physiological condition of the patient and may for example be a pressure signal, a motion signal or an electrical signal, for example relating to cardiac activity, in particular in the shape of an electrocardiogram (ECG). The physiological signal may be measured by the implantable medical device itself using a suitable sensor device of the implantable medical device, or may be received from another implantable device. In the latter case the implantable medical device may for example be a monitoring device or a recording device, such as a loop recorder, configured to record and transmit signal information to an external device.

An implantable medical device comprises a processing device in the form of an electronics unit, which serves to perform a function in an active operational state of the medical device, for example a measurement function. To operate the processing device, the implantable medical device comprises an energy storage element, particularly in the form of an electric battery, which feeds the processing device and supplies it with power in its operational state.

An implantable medical device should usually remain in a patient after implantation for a long period of time, for example several years, which requires that the energy storage has a corresponding capacity to supply the functional equipment. However, because such a medical device should, for example, have a small shape in order to be able to implant the medical device into small blood vessels, for example within the heart or within an artery, the available space for the energy storage element and thus also the capacity of a battery realizing the energy storage is limited.

From the desire to miniaturize a battery for use in implantable medical devices it follows that the power consumption of the medical device should be low. For this it is desirable that functions performed by the implantable medical device are carried out in an energy efficient manner, such that a load on the energy storage of the implantable medical device is reduced.

This applies also to a data transmission for transmitting data from the implantable medical device to an external device, such as a programmer device, a home monitoring device or another external device such as an external computer or a server of a medical information system. Generally, processes involved with a data transmission should operate in an energy-efficient manner, wherein at the same time data relating to a physiological signal should be transmitted in a quality allowing for an adequate processing by the external device.

Generally, within an implantable medical device a physiological signal is digitized and processed for transmission to an external device. For transmission the signal may be compressed, hence reducing the amount of data which needs to be sent to the external device. Compression methods herein are generally grouped into lossy and lossless methods. A lossy compression reduces the fidelity of the physiological signal, whereas a lossless compression retains the original signal fidelity while still achieving compression, but coming potentially at the expense of increased processing requirements and potentially a less effective compression.

U.S. Pat. No. 5,836,982 and its counterpart European published patent application EP 0 884 851 A2 describe a system and method of non-linear sampling of an analog signal, and for data compression, to provide overall compressed digital representatives of a physiological signal obtained in a battery powered device such as an implantable pacemaker. Non-linear sampling is provided by generating a time varying threshold signal against which the analog signal is compared every clock sample, with a sample being skipped if the input analog signal does not exceed the threshold signal. The non-linearly sampled data is compressed using lossless techniques for compressing both amplitude data and time data representative of skipped samples. The time data is a signal indicative of a lapsed time, which may be compressed by using a fixed Huffman code table.

SUMMARY OF THE INVENTION

It is an object of the instant invention to provide an implantable medical device as well as an external device and a method for operating the implantable medical device which allow for an efficient data transmission from the implantable medical device to the external device.

With the above and other objects in view there is provided, in accordance with the invention, an implantable medical device, comprising:
  an electronic processing device configured for processing a physiological signal, a memory, and a communication device configured for communication with an external device;
  the processing device including a coding module for coding the physiological signal to generate an output signal for transmission by the communication device to the external device;

the coding module being configured to encode the physiological signal using at least one fixed Huffman code table stored in the memory to generate the output signal.

In other words, the coding module is configured to encode the physiological signal using at least one fixed Huffman code table stored in the memory device to obtain the output signal.

Within the implantable medical device a physiological signal, obtained from a sensor device of the implantable medical device or from another implantable device, is processed for transmission towards an external device. The external device is generally located outside of a patient. For the transmission, herein, the physiological signal, for example a pressure signal, an accelerometer signal, or an electrocardiogram (ECG) signal, is encoded using a coding module of the processing device, the coding module providing for a compression of the physiological signal for transmission towards the external device.

Herein, the coding module is configured to apply a lossless compression by using at least one fixed Huffman code table stored in a memory device of the implantable medical device for encoding the physiological signal.

When in this context it is referred to a physiological signal, it herein is assumed that the physiological signal is sensed by a sensor device which may be part of the implantable medical device itself or which may be part of another implantable device which may forward the sensed signal to the implantable medical device, which in this case for example may be an implantable monitoring device or a recording device, such as a loop recorder. The physiological signal, as obtained from the sensor device, is digitized and potentially further processed in the implantable medical device prior to the encoding by the coding module. The physiological signal hence relates to measurement data as obtained from a sensor device and as being indicative of a physiological condition of the patient.

Within a Huffman coding method, generally samples which occur more often in a signal stream are encoded using shorter codewords in comparison to samples which appear less frequently. In a traditional Huffman coding scheme, herein, a Huffman code table is adaptively generated by storing signal data and by processing the signal data in order to sort values of signal samples by their frequency of occurrence. For example, within a traditional Huffman coding scheme a fixed number of samples, e.g. 1028 ECG samples, may be stored in memory, upon which the samples are sorted based on their frequency of occurrence. The most frequent signal value is then represented by the shortest code, the lengths of the codewords for the signal values increasing with decreasing frequency of occurrence. The codewords are generated for example using a tree-building algorithm and are stored in a Huffman code table. By replacing the (digitized) signal values by the codewords, a compression for signal transmission is achieved.

Generating a Huffman code table in a traditional Huffman coding scheme consumes computational power and hence energy. For this reason, in the instant approach a fixed Huffman code table is used for encoding the physiological signal, the fixed Huffman code table being stored in the memory device of the implantable medical device and hence being fixed, i.e., the Huffman code table is not adaptively changed during operation by the device. In the instant case, hence, the Huffman code table is not adaptively generated based on an actually obtained signal, but is generated beforehand, for example offline in an initial calibration procedure using training data, in order to then store the fixed Huffman code table in the implantable medical device. Hence, during actual operation of the implantable medical device no computational load arises for generating the Huffman code table, but rather for the encoding it is referred to the fixed Huffman code table as stored in the memory device of the implantable medical device, which increases the computational efficiency of the implantable medical device and may allow for a real-time processing of physiological signal data.

In addition, because a fixed Huffman code table is used for encoding the physiological signal, the complexity of processing within the implantable medical device is reduced.

For generating the fixed Huffman code table offline prior to actual operation of the implantable medical device, training data may be used which closely resembles physiological signal data as expected during actual operation of the implantable medical device. For example, if the physiological signal to be processed by the implantable medical device relates to electrocardiogram signals, the training data is composed of electrocardiogram signals resembling data expected during actual operation in terms of amplitude, noise, rhythm type and the like. The fixed Huffman code table is then produced using a suitable tree-building algorithm for sorting signal values and by assigning codewords to signal values in dependence on their frequency of occurrence. The code table produced offline in this way is then transferred to the implantable medical device and is stored within the memory device of the implantable medical device.

By using a fixed Huffman code table for the encoding within the implantable medical device during actual operation, also the efficiency of data transmission can be increased, because both the implantable medical device and the external device are in possession of the same code table, such that the Huffman code table does not need to be transmitted from the implantable medical device to the external device, as it would have to be in case the Huffman code table would be adaptively generated within the implantable medical device. Enhanced transmission efficiency allows an increase of the amount of physical data per transmission and/or time, since the data space that would have been required for the code table can now be used to store additional physical data, for example.

In one embodiment, the physiological signal is an electrocardiogram signal, an accelerometer signal, or a pressure signal. The physiological signal may be obtained from a sensor device which is part of the implantable medical device, or which is part of another implantable device which is in communication connection with the implantable medical device.

In one embodiment, the memory device stores multiple different fixed Huffman code tables, wherein the coding module is configured to encode the physiological signal using at least one of the multiple different Huffman code tables. The fixed Huffman code tables are generated offline before actual operation of the implantable medical device using sets of training data, wherein different sets of training data may relate to different types of physiological signals, such as an electrocardiogram signal, a pressure signal, and an accelerometer signal, or to a particular type of a physiological signal, but different states of the physiological signal. Based on the different training data sets different Huffman code tables are generated and are stored in the implantable medical device, such that the encoding of the physiological signals may take place using the different Huffman code tables.

If the different Huffman code tables relate to a physiological signal of a particular type, but different states of the type of physiological signal, the physiological signal may for example be an electrocardiogram (ECG) signal, wherein the different states of the ECG signal may relate to for example a ventricular tachycardia ECG signal, a noisy ECG signal, a railed ECG signal, and a sinus ECG signal. Hence, in different physiological states of a patient different signals generally relating to the same type of signal, e.g. an electrocardiogram signal, may occur. Training data may relate to these different states and hence may allow for generating Huffman code tables allowing for an efficient compression of the physiological signal in different states.

If multiple Huffman code tables are stored within the memory device, for the encoding one of the Huffman code tables may be selected prior to the encoding, for example based on measurement parameters allowing to identify a suitable Huffman code table, e.g., based on a particular physiological state. In an alternative approach, all or at least a subgroup (more than one) of the multiple stored Huffman code tables may be used to encode the physiological signal, such that multiple coded signals are obtained. Within the coding module it then may be selected which of the coded signals to choose and transmit as the output signal, for example based on a compression efficiency. For example, that coded signal may be chosen as the output signal which exhibits the largest compression ratio and hence corresponds to the smallest amount of data to be transmitted.

In one embodiment, the coding module comprises an accumulator for accumulating coded signal samples prior to transmitting at least some of the coded signal samples as the output signal. The coding may take place using the at least one fixed Huffman code table on a sample-by-sample basis. Coded signal samples are then stored in the accumulator, which functions as a buffer, such that data transmission may take place once a predefined amount of data has been collected within the accumulator.

The accumulator in particular may serve to store coded signal samples which have been coded using different Huffman code tables, in order to then select which group of the coded signal samples coded by means of a particular Huffman code table shall be transmitted as the output signal.

In one embodiment, the communication device is configured to transmit the output signal in a data message to the external device, wherein the data message comprises a header including information relating to the at least one fixed Huffman code table used to encode the physiological signal. Because a fixed Huffman code table is used for the encoding of the physiological signal, the actual Huffman code table does not need to be transmitted from the implantable medical device to the external device, as both the external device and the implantable medical device are in possession of the Huffman code table as it has been generated beforehand. As for example multiple Huffman code tables may be stored within the implantable medical device and may be used to encode the physiological signal in order to then choose, for example based on an achieved compression ratio, the coded signal associated with a particular Huffman code table, it may however be identified in the header using a suitable identifier by means of which Huffman code table the transmitted, coded signal samples are coded, such that the external device receiving the transmitted output signal is enabled to decode the coded signal samples.

The identifier used for identifying the Huffman code table may be a bit word having a predefined length. If for example four different Huffman code tables are stored within the implantable medical device, a bit word having a length of two bits may be sufficient to identify the Huffman code table used for the encoding.

In one embodiment, the coding module comprises a variability reduction stage for reducing a signal variability of the physiological signal prior to encoding the physiological signal. Generally, a physiological signal, such as an electrocardiogram signal, may have a rather strong signal variability. However, by using signal processing the variability of the signal values of the physiological signal may be reduced, such that a compression efficiency using a fixed Huffman code table may be increased, because the frequency of occurrence of signal values is increased. The variability reduction herein shall be reversible in that the original signal, which is not reduced in its variability, may be re-produced at the external device.

For example, a delta encoding method may be used for a reversible variability reduction. Within the delta encoding a processed signal sample is computed based on a difference of at least two signal samples of the physiological signal. For example, for the delta encoding the difference between the actual signal sample and the preceding example may be computed, such that the processed signal sample indicates the change from the preceding signal sample to the actual signal sample.

In a header of a data message also information relating to a variability reduction method may be included. For example, if a delta encoding method is used, a reference value from which the delta encoding starts may be transmitted within the header, such that based on the reference value and the difference signals obtained within the delta encoding the actual, non-processed signal may be reconstructed.

In one embodiment, a single-stage variability reduction may be employed. In another embodiment, multiple stages of variability reduction may be applied, wherein in the multiple stages the same variability reduction method, such as for example a delta encoding, or multiple different variability reduction methods may be applied.

In one embodiment, event data may be included in a data sequence representing the encoded physiological signal. For example, an event may be identified by a certain codeword, which may be included in a data sequence relating to the physiological signal. For example, an event could relate to a ventricular sense event, which may be identified using a suitable, associated codeword which is included in the data sequence.

For example, in a scheme of including an event identifier in a data sequence representing the encoded physiological signal, compression may be momentarily paused if an event of interest is detected by the implantable medical device. At this point a number of bytes may be inserted into the data sequence relating to the (compressed) physiological signal to represent the event of interest. In addition to event bytes, information bytes may be inserted relating e.g. to the event (for example identifying the number of event bytes inserted in the data sequence), or relating to the compression, e.g. by identifying the state of compression prior to pausing the compression. In addition to the event bytes and the information bytes, an event codeword may be inserted into the data sequence to identify the event, upon which compression may be resumed and hence further compressed, coded physiological signal samples are included into the data sequence. The insertion of the event bytes, the information bytes and the event codeword may in particular be timed between two consecutive signal samples such that no signal sample is lost.

In another aspect, an external device for communicating with an implantable medical device comprises an electronic processing device configured for processing a received signal obtained from the implantable medical device. The processing device comprises a decoding module for decoding the received signal. The decoding module is configured to decode the received signal using at least one fixed Huffman code table to obtain a decoded signal.

In yet another aspect, a method for operating an implantable medical device comprises: processing a physiological signal using an electronic processing device of the implantable medical device; communicating with an external device using a communication device of the implantable medical device, wherein the processing device comprises a coding module for coding the physiological signal to obtain an output signal for transmission by the communication device to the external device; and encoding the physiological signal, by the coding module, using at least one fixed Huffman code table stored in a memory of the implantable medical device to obtain the output signal.

The advantages and advantageous embodiments described above for the implantable medical device equally apply to the external device and the method, such that it shall be referred to the above.

Other features which are considered as characteristic for the invention are set forth in the appended claims.

Although the invention is illustrated and described herein as embodied in an implantable medical device with a coding module, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 6 shows a schematic drawing of the implantable medical device in communication with an external device;

FIG. 7 shows an example of a Huffman code table; and

FIG. 8 shows a schematic drawing of a coding scheme involving multiple fixed Huffman code tables.

DETAILED DESCRIPTION OF THE INVENTION

Figure 1:
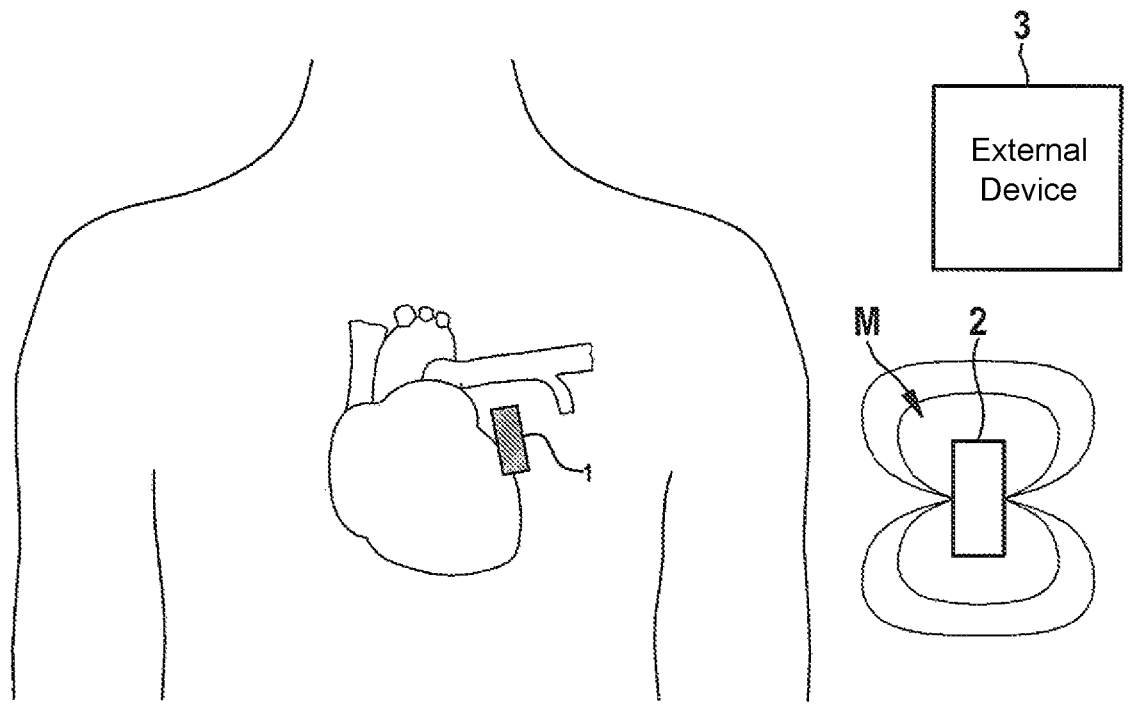
FIG. 1 shows a schematic view of a medical device implanted in a patient, along with an external signal source and an external monitoring device.

Referring now to the figures of the drawing in detail and first, particularly, to FIG. 1 thereof, there is shown a schematic view of an embodiment of an implantable medical device 1, which may be configured for example as a sensing system for measuring a physiological signal, for example a blood pressure or a blood flow, or a stimulation device such as a pacemaker device or the like. The implantable medical device may generally be implanted in a vessel of a patient, such as within the patient's heart or within an artery or at another location within the patient.

The medical device 1 is used to perform a function in a patient over a prolonged period of time, such as a measurement function or a cardiac or neuronal stimulation function for the purpose of therapy. For example, the medical device 1 shall remain in a patient for multiple years in order to record measurement data during the lifetime of the medical device 1 and to communicate with an external device 3. In that case, the measurement data may be used to diagnose or monitor the condition of the patient.

Figure 2:
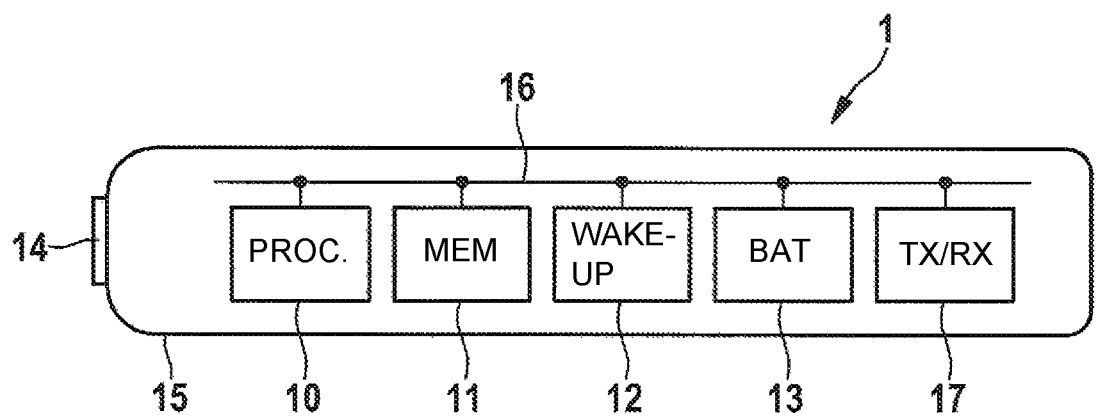
FIG. 2 shows a schematic view of an implantable medical device.

Such a medical device 1 should be small in size. As schematically shown in FIG. 2, the medical device 1, for example, comprises a housing 15, which, in one embodiment, may comprise a substantially cylindrical housing shape, with a length between 10 mm and 40 mm and a diameter of, say, between 3 mm and 10 mm. Other dimensions are also conceivable and possible.

Such a medical device 1 comprises, in the illustrated exemplary embodiment, an electronic processing device 10 which is formed, for example, by a processor and serves to perform a predetermined function, for example a measuring function or a therapy function. The medical device 1 in addition comprises a memory 11, e.g. in the form of a RAM (Random Access Memory), a wake-up device 12, an energy storage 13, for example in the form of a battery, and a communication device 17 for communicating with the external device 3. The different functional units are encapsulated together in the housing 15 in a fluid-tight manner and are interconnected for example by a bus system 16 for data exchange between the different devices.

The medical device 1 in addition, in the illustrated embodiment, comprises for example a measurement sensor 14, which is used together with the processing device 10 to perform a measurement in order to record measurement data, for example to measure a physiological signal such as a pressure signal within a patient's vessel or an electrocardiogram (ECG) signal. A measurement may be performed over a predetermined period of time, for example a few seconds or a few minutes, the measurement data being stored e.g. temporarily in the memory 11 during a measurement and communicated to the external device 3 via the communication device 17.

Because the medical device 1 has small dimensions, the size of the energy storage 13 is also necessarily limited. Because the medical device 1 is to remain in a patient and be operative for a prolonged period of time, for example several years, it is desired that the medical device 1 operates energy-efficiently, thus requiring little power, but still functions reliably to perform one or more predetermined functions.

In order to reduce the energy consumption of the medical device 1, in the embodiment of FIG. 2 the processing device 10 does not operate continuously and at all times, but is only switched from a switched-off state to an operational state when required in order to carry out a function in the operational state. In the switched-off state the processing device 10 is shut down and requires no or only very limited power, so that in the switched-off state of the processing device 10 the system of the medical device 1 exhibits a low overall power consumption. Herein, in order to transfer the processing device 10 from the switched-off state to the operational state, the wake-up device 12 is provided, which serves to switch on the processing device 10 based on a signal provided from an external activator device 2 such as a permanent magnet device (see FIG. 1).

The communication device 17, in cooperation with the processing device 10, serves to communicate with the external device 3 in order to transmit data towards the external device 3 and to receive data from the external device 3. In particular, the processing device 10 shall process data relating to physiological signals for transmission by means of the communication device 17, such that the data may be transmitted towards the external device 3, for example using telemetry or another known communication technology for communication between an implantable medical device 1 and an external device 3, such as a programmer device, a home monitoring device or a medical information system provided for collecting and viewing data obtained from an implantable medical device 1.

Generally, for the communication with the external device 3, data relating to a physiological signal is compressed, wherein it is proposed in the instant text to use a lossless compression scheme involving a fixed Huffman code table stored in the memory device 11 of the implantable medical device 1.

Making use of a fixed Huffman coding scheme, a physiological signal is encoded by representing signal values using codes as defined in a fixed Huffman code table. Instead of transmitting a signal value as such in digitized form, a corresponding code as defined in the Huffman code table is transmitted, wherein the Huffman code table is constructed such that, generally, values which occur more frequently are represented by a shorter code in comparison to values which appear less frequently.

The fixed Huffman code table is stored in the memory device 11 of the implantable medical device 1. The fixed Huffman code table herein is generated offline prior to the actual operation of the implantable medical device 1 and is transferred to and stored in the implantable medical device 1. The fixed Huffman code table is generally not adapted during the operation of the implantable medical device 1.

The fixed Huffman code table is for example, in an initial calibration procedure, generated using a set of training data relating to the physiological signal which shall be encoded using the fixed Huffman code table. If the physiological signal is for example an electrocardiogram signal, the training data comprises electrocardiogram signals which resemble closely, i.e. in terms of amplitude, noise, rhythm and the like, to the physiological signal as it can be expected during actual operation of the implantable medical device 1. For the generation of the Huffman code table, herein, signal values are sorted using a tree-building algorithm in order to assign codes to the signal values in dependence on their frequency of occurrence, such that those signal values which occur most frequently receive shorter codes, and signal values which appear less frequently obtain longer codes.

Because a fixed Huffman code table is used, computational efficiency for the processing within the implantable medical device 1 is improved, in that a computational load for the implantable medical device 1 is reduced. In particular, because a fixed Huffman code table as stored in the memory device 11 is used for the compression, no adaptive generation of a Huffman code table within the implantable medical device 1 is required, allowing for a fast, real-time processing.

Furthermore, because a fixed Huffman code table is used, an algorithm for the processing within the processing device 10 may have a reduced complexity.

In addition, transmission efficiency is improved, as no data relating to an actually generated Huffman code table needs to be transmitted from the implantable medical device 1 to the external device 3, as it would be the case if using a traditional Huffman coding scheme in which a Huffman code table is generated online adaptively based on actual measurement values. Enhanced transmission efficiency allows an increase of the amount of physical data per transmission and/or time, since the data space that would have been required for the code table can now be used to store additional physical data, for example.

Figure 3:
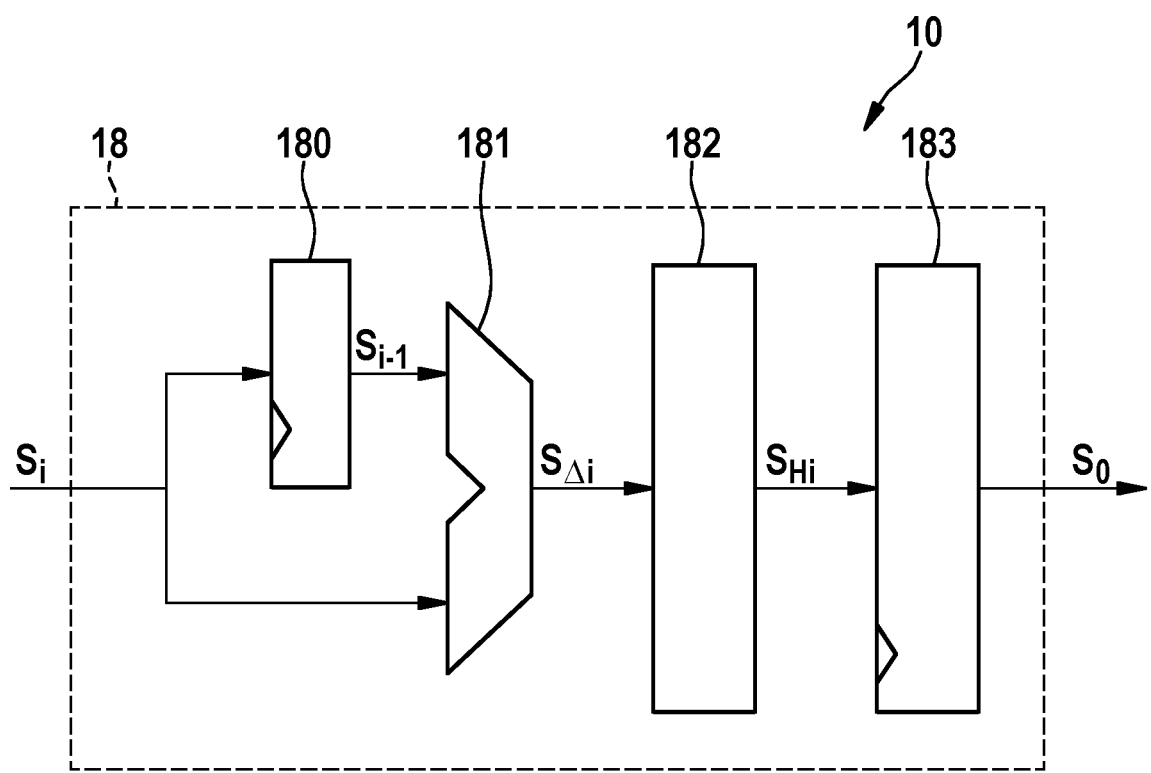
FIG. 3 shows a schematic drawing of a coding module of the implantable medical device.

Referring now to FIG. 3, for encoding a physiological signal the processing device 10 comprises a coding module 18, for example implemented in a modular fashion by a software module. The coding module 18 serves to process samples $S_i$ of a physiological signal to generate an output signal $S_O$ for transmission using the communication device 17.

Input samples $S_i$ are, for example, received from another processing stage of the processing device 10 and represent a physiological signal in digitized form. The output signal $S_O$ is output to a subsequent stage for transmission using the communication device 17.

Within the coding module 18, a signal sample $S_i$ is input to a register 180, which serves to buffer the signal sample $S_i$. The signal sample $S_i$ is furthermore input to a variability reduction stage 181, together with a previous sample $S_{i-1}$ from the register 180, the previous sample $S_{i-1}$ representing the sample value at the previous clock cycle. The variability reduction stage 181 may for example implement a delta encoding, in which the difference between the actual signal sample $S_i$ and the previous signal sample $S_{i-1}$ is determined and output as a processed sample $S_{\Delta i}$.

The processed sample $S_{\Delta i}$ hence relates to the difference between actual current sample $S_i$ and the previous sample $S_{i-1}$. In this way the variability of the signal may be reduced. If the physiological signal represented by the signal samples for example is an electrocardiogram signal at baseline, the samples may have time varying values around baseline, for example having the shape of a sequence like [−2, −1, 0, 1, 2, 2, 1, 0, −1, −2]. In this sequence, five different values occur (i.e., −2, −1, 0, 1, 2), wherein each of the signal values has an equal frequency of occurrence (⅕). Using delta encoding, the sequence may be processed to become [1, 1, 1, 1, 0, −1, −1, −1, −1]. In this sequence three different values occur (i.e., −1, 0, 1), the values of 1 and −1 having a greater frequency of occurrence than the value 0 (⅘ in comparison to ⅑).

By reducing the variability of the signal in the variability reduction stage 181, an improved compression efficiency can be achieved using a Huffman coding scheme. Generally, by decreasing the signal variability, the frequency of occurrence for particular signal values can be increased, hence allowing for an efficient coding and compression using a Huffman coding scheme.

The variability reduction in the variability reduction stage 181 is fully reversible in that the original non-reduced signal may be reconstructed from the processed signal.

Following the variability reduction stage 181, the processed samples $S_{Ai}$ are encoded using a fixed Huffman code table in the table look-up stage 182 by assigning a code to a sample $S_{Ai}$, hence obtaining a coded sample $S_{Hi}$. The coded samples $S_{Hi}$ are forwarded to an accumulator 183, which serves to buffer the coded signal samples $S_{Hi}$ and output the output signal S0 assembled from the buffered samples $S_{Hi}$.

Using a scheme of this kind, an efficient compression can be achieved, as illustrated in the diagrams of FIGS. 4A, 4B and FIGS. 5A, 5B.

Figure 4A:
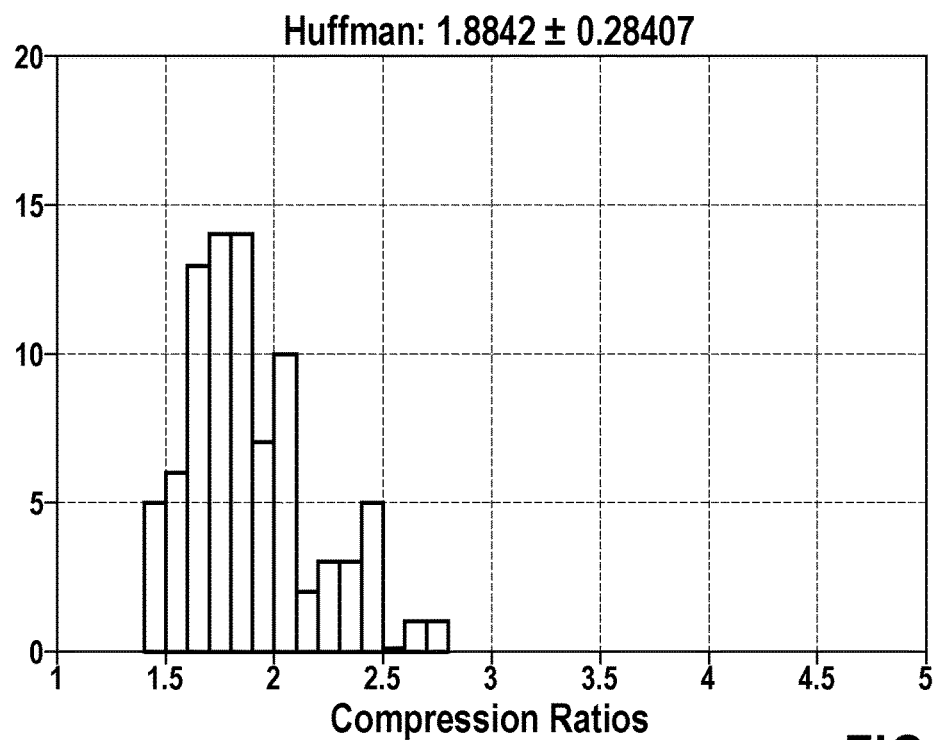
FIG. 4A shows a graphical representation of compression ratios for electrocardiogram signals, using a traditional Huffman coding scheme.

FIG. 4A herein shows a histogram of compression ratios for 84 electrocardiogram signals when using a traditional Huffman coding scheme employing adaptive Huffman code tables generated on the fly based on the actual signal values.

Figure 4B:
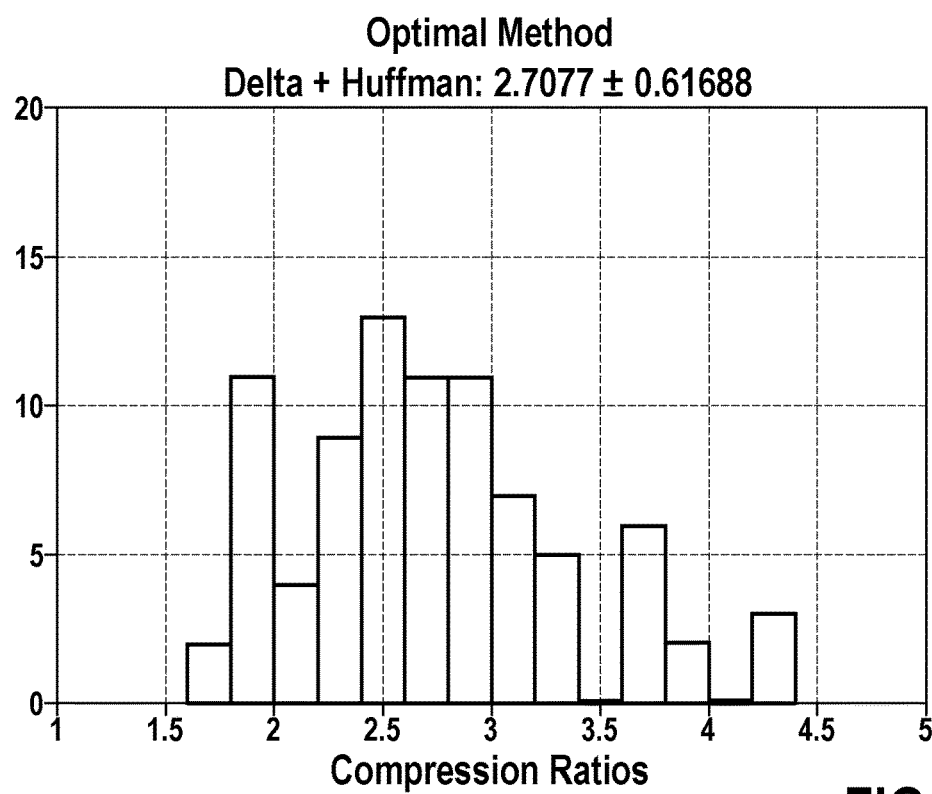
FIG. 4B shows a graphical representation of compression ratios, when using the traditional Huffman coding scheme of FIG. 4A and in addition using, prior to the coding, a variability reduction method.

FIG. 4B shows a histogram of compression ratios of the electrocardiogram signals when in addition employing a delta encoding scheme in order to reduce the variability of the signals.

Figure 5A:
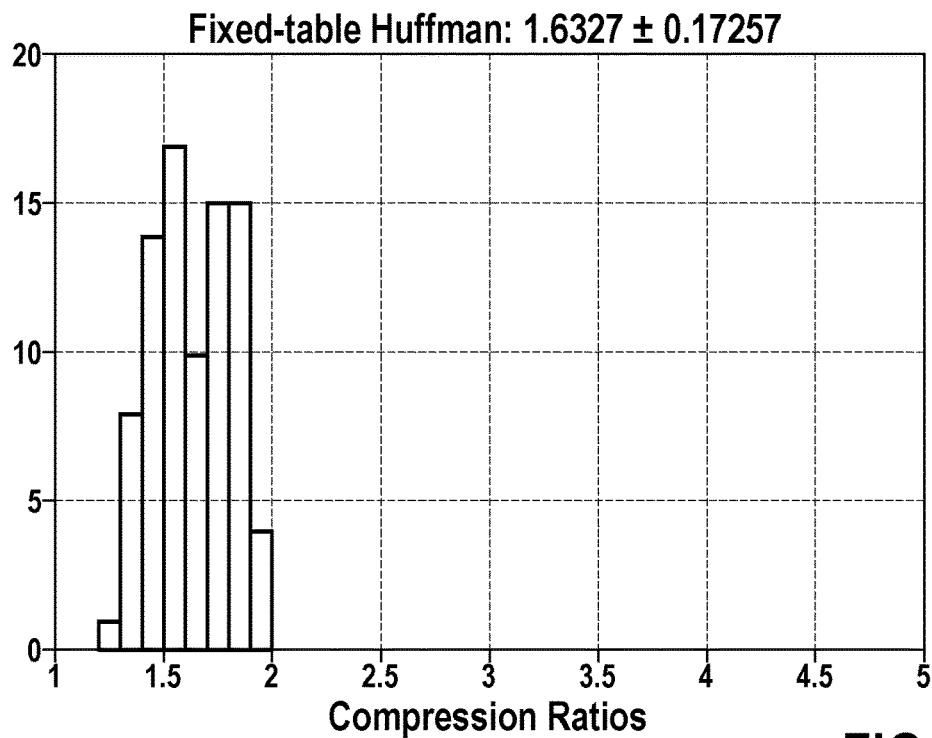
FIG. 5A shows a graphical representation of compression ratios for electrocardiogram signals, using a fixed Huffman coding scheme.

FIG. 5A, in comparison to FIG. 4A, shows a histogram of compression ratios for the 84 echocardiogram signals when using a fixed Huffman coding scheme using a fixed Huffman code table generated offline beforehand. As can be seen in comparison to FIG. 4A, the compression ratios which are obtained are generally smaller for the fixed Huffman coding scheme, hence illustrating a reduced compression efficiency.

Figure 5B:
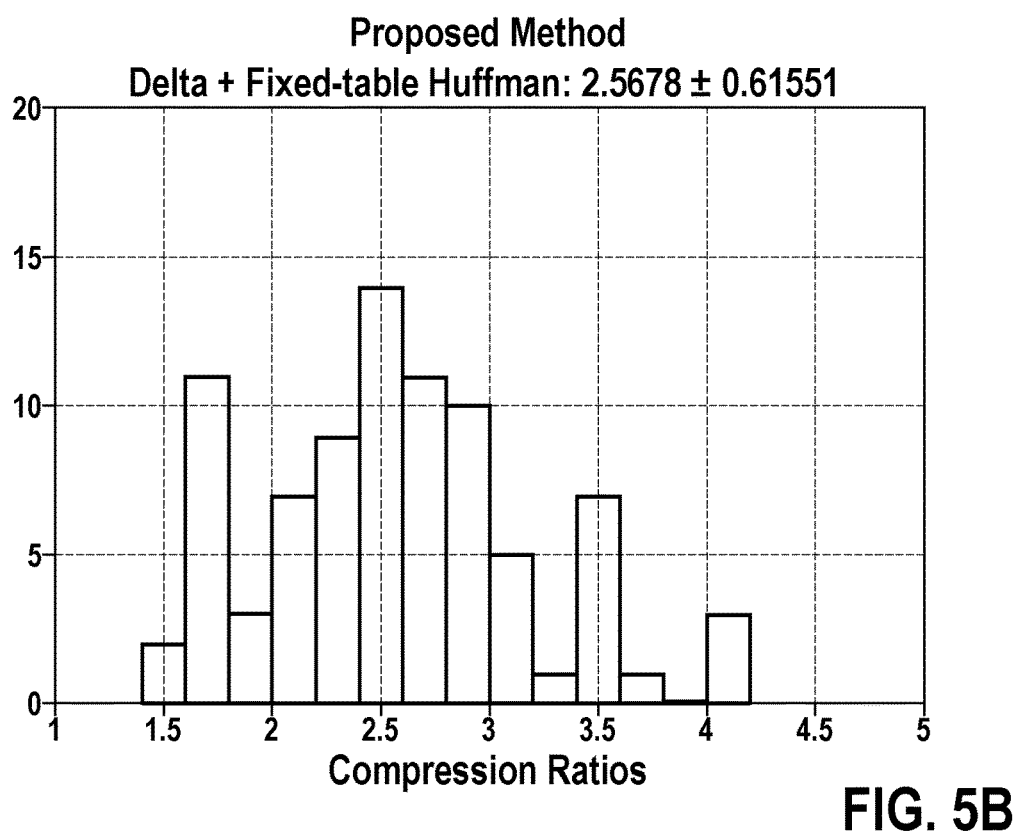
FIG. 5B shows a graphical representation of compression ratios, when using the fixed Huffman coding scheme of FIG. 5A and in addition using, prior to the coding, a variability reduction method.

FIG. 5B however shows a histogram of compression ratios for the electrocardiogram signals when in addition employing a delta encoding scheme. When comparing FIG. 4B and FIG. 5B it can be seen that the compression ratios are comparable, indicating hence that—when employing a delta encoding together with a fixed Huffman coding scheme—compression ratios comparable to a traditional Huffman coding method can be obtained, the fixed Huffman coding scheme however offering advantages in computational efficiency and reduced complexity.

Referring now to FIG. 6, the processing and coding takes place in the coding module 18, which may be implemented in the processing device 10 and which outputs the encoded output signal $S_O$ to the communication device 17 for transmission towards the external device 3. The transmission takes place in a data message D comprising a header H and a body B, the encoded signal values being inserted into the body B and the header H carrying information for example relating to the used Huffman code table and to the reversible variability reduction, such as for example a reference value representing a start value for the delta encoding.

The body B generally includes the encoded signal values as obtained after compression. In addition, however, also event-related data may be included in a data sequence of compressed physiological signal samples. Herein, within an event-detection scheme a special codeword denoted as event codeword may be inserted into the compressed signal to signify a special event or marker, such as the identification of a point of interest in the signal. As a specific example, a special event or marker could be a ventricular sense event in the compressed ECG signal. The event codeword is reserved in the fixed Huffman code table, and therefore cannot be used to represent a compressed signal value.

An event-detection scheme may work as follows. When an event of interest is detected by the implantable medical device 1, the compression of the signal is paused momentarily. At this point, a number of bytes can be inserted into the compressed data stream to represent the event(s) of interest. In addition to the event bytes, a number of information bytes can also be inserted into the data-stream while compression is paused. The information bytes can represent, as examples, additional information about the event bytes (including the number of event bytes), or information about the state of compression prior to pausing compression. Following insertion of the event and information bytes, the event codeword is inserted to the compressed data stream, and compression of the signal is resumed. The insertion of the event bytes, information bytes, and the event codeword is timed between two consecutive signal samples such that a signal sample is not lost.

Such a scheme may provide flexibility for event detection in that the event payload that precedes the codeword can represent any event. The addition of new events of interest (e.g., via a device software update) does not require modification of the fixed Huffman code table, as only a single codeword reserved from use in the fixed Huffman code table is needed to signify the occurrence of an event.

At the external device 3, which generally is located outside of the patient P, the data message D is received and processed using a processing device 30 and a decoding module 31. The external device 3 decodes the received signal to obtain the encoded signal samples, and reverses the variability reduction, for example by carrying out a summation of the difference signal as it is obtained after decoding and as it has been encoded following the delta encoding within the implantable medical device 1. A signal corresponding to the original physiological signal hence is reconstructed in a lossless fashion at the external device 3.

In particular, upon receipt of the data message D containing the header H and the compressed signal data in the body B, the decoding device 31 can decode the signal properly and recover the original lossless signal. First, the compressed data is decompressed using the applicable fixed Huffman code table. This involves finding codewords in the compressed data that match codewords in the code table, and outputting the corresponding decompressed data value. This process also includes recognizing events that are identified by the event codeword in the data stream. Next, if a variability-reduction processing step was performed by the implantable medical device 1, the uncompressed data values will actually represent the processed signal. In this case, the decoding device 31 will then use information in the received header H to reverse the variability-reduction step. Following reversal of the variability-reduction step, the output signal will match the original signal as measured and digitized by the implantable medical device 1. This output signal can then be displayed and/or stored on the external device 3 or forwarded to another device for further processing.

Referring now to FIG. 7, within a Huffman code table T signal values (in the left-hand column of the table T) are associated with codes (in the right-hand column of the table T). Herein, generally the table T is constructed such that a signal value which has the greatest frequency of occurrence is associated with the shortest code, and in turn signal values having a lesser frequency of occurrence obtain longer codes. In this way it can be achieved that the most frequent signal values are transmitted using short codes, hence allowing for an efficient compression and transmission of a signal.

Referring now to FIG. 8, in one embodiment, multiple Huffman code tables $T_1, T_2, T_3 \ldots T_N$ may be stored within the memory device 11 for processing the signal samples.

Herein, in one embodiment, the processed signal samples $S_{Ai}$ as obtained after the variability reduction stage 181 are, within the table look-up stage 182, encoded using the different Huffman code tables $T_1, T_2, T_3 \ldots T_N$ to obtain different streams of encoded samples $S_{H1i}, S_{H2i}, S_{H3i} \ldots S_{HNi}$, which are forwarded to the accumulator 183 and are temporarily stored within the accumulator 183. Based on stored sequences of encoded signal samples $S_{H1i}$, $S_{H2i}$, $S_{H3i} \ldots S_{HNi}$ it is selected which sequence associated with a particular Huffman code table $T_1, T_2, T_3 \ldots T_N$ is used for transmission as the output signal $S_O$, wherein the selection takes place based on compression efficiency, i.e., that sequence is transmitted as the output signal $S_O$ which exhibits the largest compression ratio.

If multiple Huffman code tables $T_1, T_2, T_3 \ldots T_N$ according to the scheme of FIG. 8 are used, additional information may be included in the header H of the transmitted data message D indicating based on which Huffman code table $T_1, T_2, T_3 \ldots T_N$ the output signal $S_O$ is encoded.

The different Huffman code tables $T_1, T_2, T_3 \ldots T_N$ may relate to different signal types, such as an electrocardiogram signal, an accelerometer signal, a pressure signal and so on. Alternatively, the different Huffman code tables $T_1, T_2, T_3 \ldots T_N$ may relate to the same signal type, for example an electrocardiogram signal, but to different physiological states, i.e. to a particular type of a physiological signal under different conditions. For example, the different Huffman code tables $T_1, T_2, T_3 \ldots T_N$ may relate to a ventricular tachycardia ECG, a noisy ECG, a railed ECG, and a sinus ECG and hence to an ECG signal in different physiological states.

Which code table is used to obtain the output signal $S_O$ in each case may be stored within the header H and transmitted to the external device 3.

By means of coding using a fixed Huffman coding table $T, T_1, T_2, T_3 \ldots T_N$ compressed signal data may be obtained in real time and may be stored within the implantable medical device 1 for transmission to the external device 3. The real-time compressed data stream herein may be diverted to multiple storage locations of arbitrary size in the implantable medical device 1. The diversion and storage into arbitrary memory spaces can occur at any time based on events or based on criteria set in the implantable medical device 1.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

Based on the above, a real-time compression of signals using fixed Huffman code tables that are generated offline and stored in an implantable medical device becomes possible. This may reduce the complexity of a compression procedure within the implantable medical device. The ability to compress in real-time may provide flexibility in storage mechanisms of the compressed data stream.

The generation of a fixed Huffman code table may be performed by using a training set of signals that resemble the type of signal to be compressed.

The use of reversible variability-reduction pre-processing steps on the signals to be compressed may improve the Huffman compression performance in general, and may make the fixed-table Huffman approach similar in performance to an optimal (traditional) Huffman approach.

A flexible event-detection scheme may be incorporated to insert events of interest into the compressed bit-stream.

A header may be incorporated with each compressed signal that assists the decoder in decompressing the signal appropriately (e.g., informational bytes to assist the decoder in reversing the variability-reduction step, which code table to use, etc.).

A use of multiple code tables may allow for a yet improved compression of different signal types or variations of a single signal type.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

The following is a list of reference numerals and symbols used in the above description of the invention with reference to the drawing figures:

1 Implantable medical device
10 Processing device
11 Memory device
12 Wake-up device
13 Energy storage
14 Sensor device
15 Housing
16 Bus system
17 Communication device
18 Coding module (encoder)
180 Register
181 Variability reduction stage
182 Table look-up stage
183 Accumulator
2 Activator device
3 External device
30 Processing device
31 Decoding module (decoder)
B Message body
D Data message
H Message header
M Magnetic field
$S_i$, $S_{i-1}$ Signal samples
$S_{Ai}$ Processed signal sample
$S_{Hi}$ Coded signal sample
$S_{H1i} \ldots S_{HNi}$ Coded signal samples
$S_O$ Output signal
T Huffman code table
$T_1 \ldots T_N$ Huffman code tables

The invention claimed is:

1. An implantable medical device, comprising:
   an electronic processing device configured for processing a physiological signal, a memory, and a communication device configured for communication with an external device;
   said processing device including a coding module for coding the physiological signal to generate an output signal for transmission by said communication device to the external device;
   said coding module being configured to encode the physiological signal using at least one fixed Huffman code table stored in said memory to generate the output signal.

2. The implantable medical device according to claim 1, further comprising a sensor device for measuring the physiological signal.

3. The implantable medical device according to claim 1, wherein the physiological signal is an electrocardiogram signal, an accelerometer signal, or a pressure signal.

4. The implantable medical device according to claim 1, wherein said memory is configured to store a plurality of different fixed Huffman code tables, and said coding module is configured to encode the physiological signal using at least one of the plurality of different fixed Huffman code tables.

5. The implantable medical device according to claim 4, wherein the plurality of different fixed Huffman code tables relate to different types of physiological signals.

6. The implantable medical device according to claim 4, wherein the plurality of different fixed Huffman code tables relate to a single type of a physiological signal, but to different states of the physiological signal.

7. The implantable medical device according to claim 4, wherein said coding module is configured to encode the physiological signal using the plurality of different fixed Huffman code tables to obtain multiple coded signals.

8. The implantable medical device according to claim 7, wherein said coding module is configured to select one of the coded signals as the output signal for transmission by said communication device.

9. The implantable medical device according to claim 1, wherein said coding module comprises an accumulator for accumulating coded signal samples prior to transmitting at least some of the coded signal samples as the output signal.

10. The implantable medical device according to claim 1, wherein said communication device is configured to transmit the output signal in a data message to the external device, the data message comprising a header including information relating to the at least one fixed Huffman code table used to encode the physiological signal.

11. The implantable medical device according to claim 1, wherein said coding module comprises a variability reduction stage for reducing a signal variability of the physiological signal prior to encoding the physiological signal.

12. The implantable medical device according to claim 11, wherein said variability reduction stage is configured to apply a delta encoding to the physiological signal, and wherein, within the delta encoding, a processed signal sample is computed based on a difference of at least two signal samples of the physiological signal.

13. The implantable medical device according to claim 1, wherein said processing device is configured to include, in a data sequence representing the encoded physiological signal, at least one event identifier.

14. An external device for communicating with the implantable medical device according to claim 1, the external device comprising:
an electronic processing device configured for processing a signal received from the implantable medical device;
said processing device including a decoding module for decoding the signal received from the implantable medical device;
said decoding module being configured to decode the signal received from the implantable medical device using at least one fixed Huffman code table to obtain a decoded signal.

15. The implantable medical device according to claim 1, wherein said coding module comprises an accumulator for accumulating coded signal samples into a predefined amount of data so that the predefined amount of data, which has been accumulated, can be subsequently transmitted together in a data transmission.

16. The implantable medical device according to claim 1, wherein said memory is configured to store a plurality of different fixed Huffman code tables relating to different types of physiological signals, and said coding module is configured to encode the physiological signal using one of said plurality of different fixed Huffman code tables relating to a type of the physiological signal being processed by said electronic processing device.

17. A method of operating an implantable medical device, the method comprising:
processing a physiological signal using an electronic processing device of the implantable medical device;
communicating with an external device using a communication device of the implantable medical device;
generating the output signal with a coding module of the processing device by encoding the physiological signal using at least one fixed Huffman code table stored in a memory of the implantable medical device, to obtain the output signal; and
transmitting the output signal with the communication device to the external device.

18. The method according to claim 17, which comprises: generating the at least one fixed Huffman code table offline and then transferring the at least one fixed Huffman code table to the implantable medical device.

* * * * *